United States Patent [19]

Blake, III et al.

[11] Patent Number: 4,562,839
[45] Date of Patent: Jan. 7, 1986

[54] SURGICAL INSTRUMENT

[76] Inventors: Joseph W. Blake, III; Paul C. DiCesare, both of 88 Main St., New Canaan, Conn. 06840

[21] Appl. No.: 456,163

[22] Filed: Jan. 6, 1983

[51] Int. Cl.⁴ .............................................. A61B 17/12
[52] U.S. Cl. .................................. 128/326; 128/334 R
[58] Field of Search ........................ 29/243.56; 72/410; 81/345; 128/325–326, 334 R; 227/DIG. 1 A, DIG. 1 B

[56] References Cited

U.S. PATENT DOCUMENTS

| | | | |
|---|---|---|---|
| 2,959,172 | 11/1960 | Held | 128/326 |
| 3,545,444 | 12/1970 | Green | 128/326 |
| 3,777,538 | 12/1973 | Weatherly et al. | 72/410 |
| 3,819,100 | 6/1974 | Noiles et al. | 227/19 |
| 3,949,924 | 4/1976 | Green | 227/132 |
| 4,196,836 | 4/1980 | Becht | 227/110 |
| 4,204,623 | 5/1980 | Green | 227/19 |
| 4,296,751 | 10/1981 | Blake, III et al. | 128/325 |
| 4,367,746 | 1/1983 | Derechinsky | 29/243.56 |
| 4,448,194 | 5/1984 | DiGiovanni et al. | 128/334 R |

FOREIGN PATENT DOCUMENTS 2044108 10/1980 United Kingdom ............... 128/326

Primary Examiner—C. Fred Rosenbaum
Assistant Examiner—Gene B. Kartchner

[57] ABSTRACT

An instrument for applying clips to a surgical site has an applicator with two jaws which are movable between open and closed positions. A mechanism is provided for feeding the respectively leading clip of a string of such clips between the jaws, whereupon the jaws are closed and the leading clip is cinched as it is being applied to the surgical site. To vary the presentation of the clip, i.e., its orientation relative to the surgical site, the mechanism is mounted so that it can turn about a longitudinal axis of the instrument. In one embodiment, a slide button is provided which can be slid forward and backward with one finger of a user, such translatory movement of the button being converted into a turning movement of the mechanism and consequently also of the clip which is being held between the anvils preparatory to its application to the surgical site. In another embodiment, turning movement is effected by rotating a knob secured to the mechanism.

6 Claims, 6 Drawing Figures

Fig. 1.
*(Prior Art)*

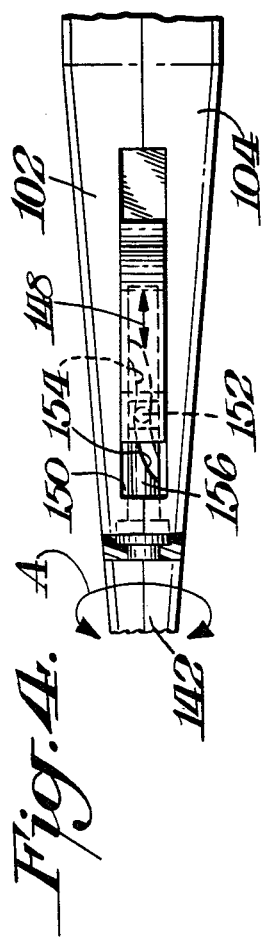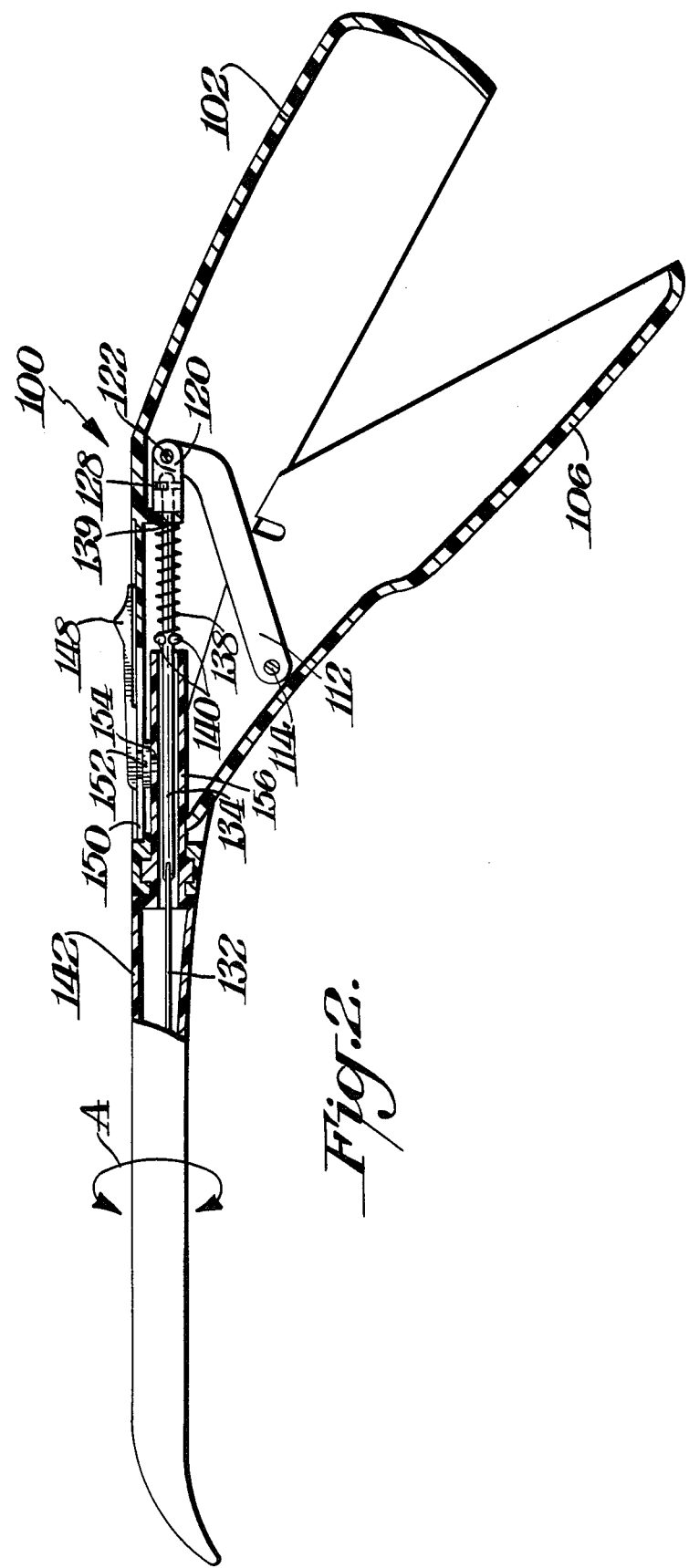

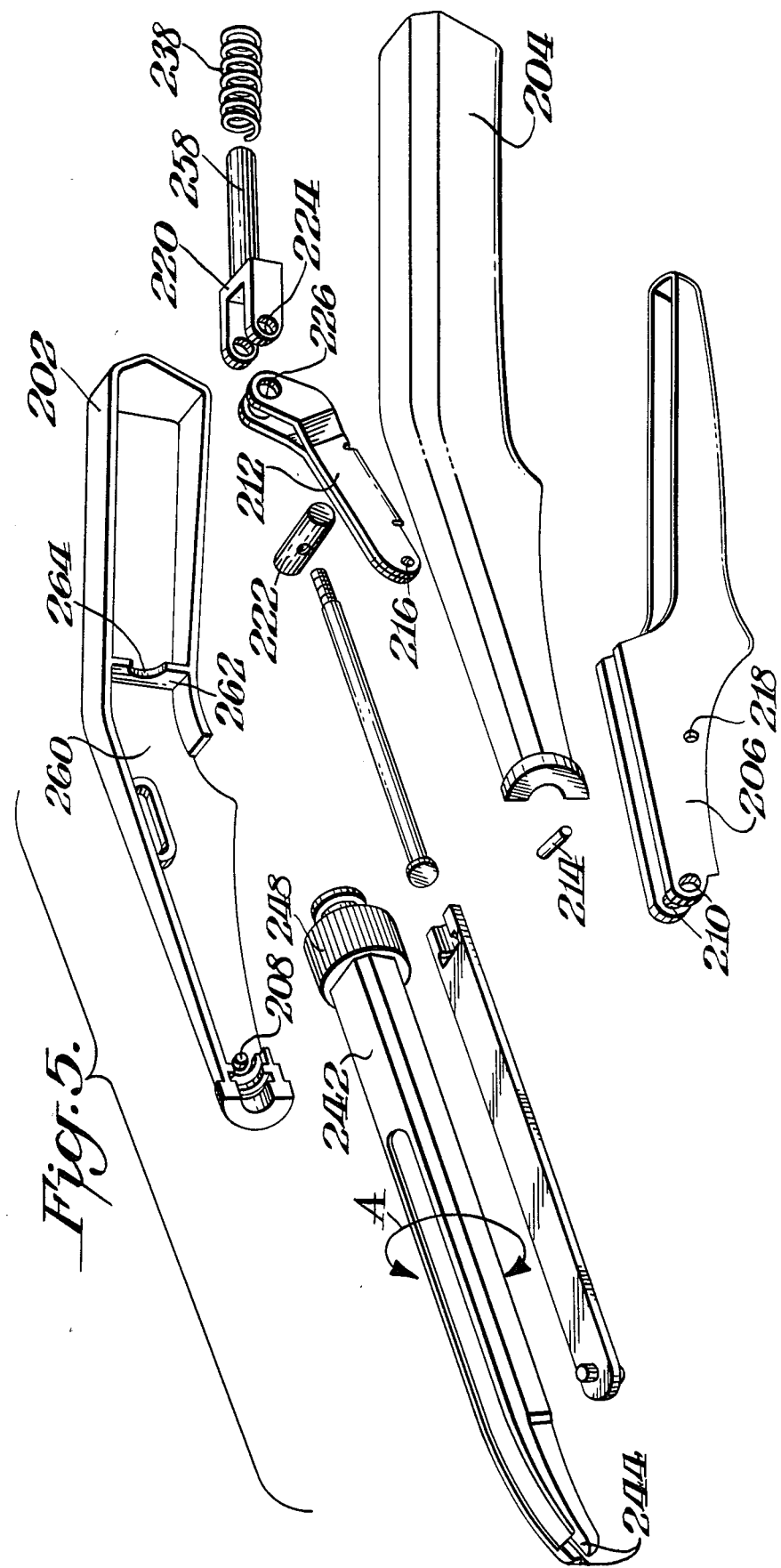

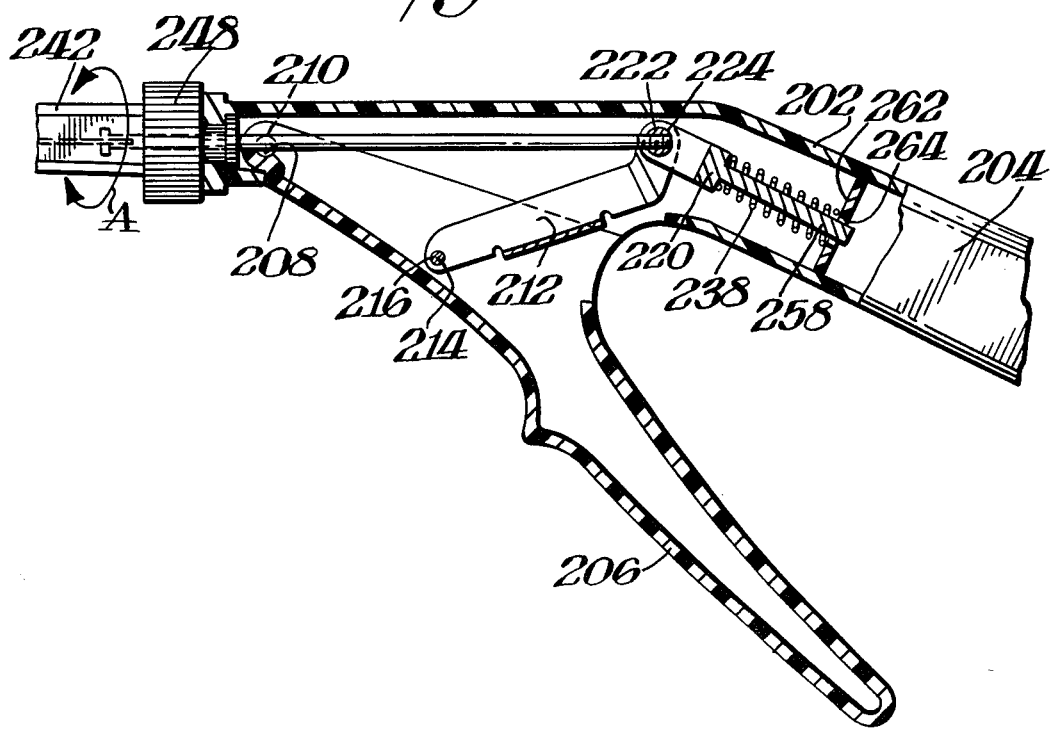

SURGICAL INSTRUMENT

BACKGROUND OF THE INVENTION

The present invention relates to a surgical instrument. More particularly, the invention relates to a ligating instrument. Still more specifically, this invention relates to a clip-dispensing and applying ligating device.

Surgical instruments of the type here under discussion are known in a variety of structural designs. For example, it is known to provide hemostatic forceps which are individually loaded with securing clips; among such clip applicators is that disclosed in U.S. Pat. No. 3,777,538, the jaws of which can be incrementally rotated about a longitudinal axis. It has also been proposed to utilize a magazine-loaded hemostatic forceps with semiautomatic clip feed and, in fact, other proposals involve the use of magazine-loaded devices with automatic clip feed.

Some of these devices are too complicated and/or difficult to use and have therefore never found any acceptance. Others work more or less well and have found acceptance in the medical profession to a greater or lesser degree.

All of the prior art instruments of the type in question have one thing in common, however; there is no way to change the presentation of the leading clip to a surgical site, i.e., its orientation relative to the site, unless the user (surgeon) changes the position of his hand in which he holds the instrument. This may, at first mention, appear to be a relatively minor matter; in point of fact, however, since much depends upon the ease and absence of fatigue with which the surgeon is able to hold his hand, it is not a minor point. Thus, should he be forced to hold his hand in a position which to him is fatiguing, he may rapidly reach the point at which his hand is no longer steady enough to apply the clips with the necessary precision.

Stapling devices are known for externally stapling or suturing the skin. In known such devices, disclosed, for example, in U.S. Pat. Nos. 3,819,100 (U.S. Pat. No. Re. 28,932), 3,949,924, 4,196,836 and 4,204,623, it is possible to rotate the staple housing about a longitudinal axis. In these devices, however, rotation of the staple housing to any degree is not readily possible by manipulation with the same hand which actuates the stapling operation. Although such stapling devices are known, no one heretofore had considered rotating the clip housing in ligating devices using openable and closable jaws.

SUMMARY OF THE INVENTION

Accordingly, it is a general object of the present invention to overcome the disadvantages of the prior art.

A more particular object of the invention is to provide an improved surgical clip-applying instrument which is not possessed of the aforementioned prior-art disadvantages.

Another object of the invention is to provide a surgical instrument of the type under discussion which permits variations in the presentation (orientation) of at least the leading clip of a string of clips relative to a surgical site without requiring concomitant change in the orientation of a user's hand holding the instrument.

Still a further object of the present invention is to provide such an instrument as outlined hereinbefore which is of relatively simple construction and therefore comparatively inexpensive and disposable.

Yet another object is to provide such an instrument which is reliable and which in use comes as close as possible to being free of malfunctions.

In keeping with these objects, and with still others which will become apparent hereinafter, one aspect of the invention resides in a surgical instrument for applying clips to a surgical site. Briefly stated, such an instrument may comprise an applicator means having a pair of cooperating jaws provided with anvils and being movable between an open and a closed position; supply means for feeding surgical clips of a string of such clips to the jaws, including means for advancing the string towards the jaws in a predetermined path for seriatim insertion of the respectively leading clip of the string between the anvils while the jaws are in the open position so as to become cinched between the anvils when the jaws move to the closed position; and mounting means mounting at least part of the supply means for angular displacement about the path so as to vary the orientation at which the leading clip is presented to the surgical site.

It is currently preferred to mount the assembly composed of the jaws, the entire magazine, i.e., the clip supply means, and the housing therefor in such a manner that they can all rotate about the longitudinal axis of the instrument, which is also about the path of movement of the clips. Further, in one embodiment, a switch or button may be provided which is slidable lengthwise of this path by finger pressure and, in so doing, effects turning, i.e., angular displacement of the assembly, in one or in the opposite direction. It is then a simple matter for the surgeon, using the same hand as that for actuation of the jaws, to change the presentation (orientation) of the leading clip relative to the surgical site merely by pushing the slide button further forwards or backwards and without having to alter the position of his hand relative to the surgical site. The possibility of undue fatigue resulting from the need to hold the instrument in what is to the surgeon an uncomfortable or inconvenient position is thereby avoided.

In a preferred embodiment, a knob of circular cross section is secured to the barrel for joint movement. Thus when the knob is turned, the barrel also turns.

An ancillary feature in this invention is to operatively connect trigger means to at least the supply means to effect operation thereof.

The novel features which are considered to be characteristic of the invention are set forth in particular in the appended claims. The improved device itself, however, together with its construction and mode of operation, as well as additional features and advantages thereof, will be best understood upon a perusal of the following detailed description of specific, although purely exemplary, embodiments with reference to the accompanying drawing.

BRIEF DESCRIPTION OF THE DRAWING

FIG. 1 is a top view, illustrating a prior art instrument known from U.S. Pat. No. 4,296,751;

FIG. 2 is a side elevational view, partly in vertical section, illustrating one embodiment of the invention;

FIG. 4 is a fragmental top plan view of the embodiment of FIG. 2;

FIG. 5 is a view similar to FIG. 3 but of a different embodiment of the invention; and FIG. 6 is a side elevational view in vertical section of the embodiment of FIG. 5.

DESCRIPTION OF PREFERRED EMBODIMENTS

Figure 3:
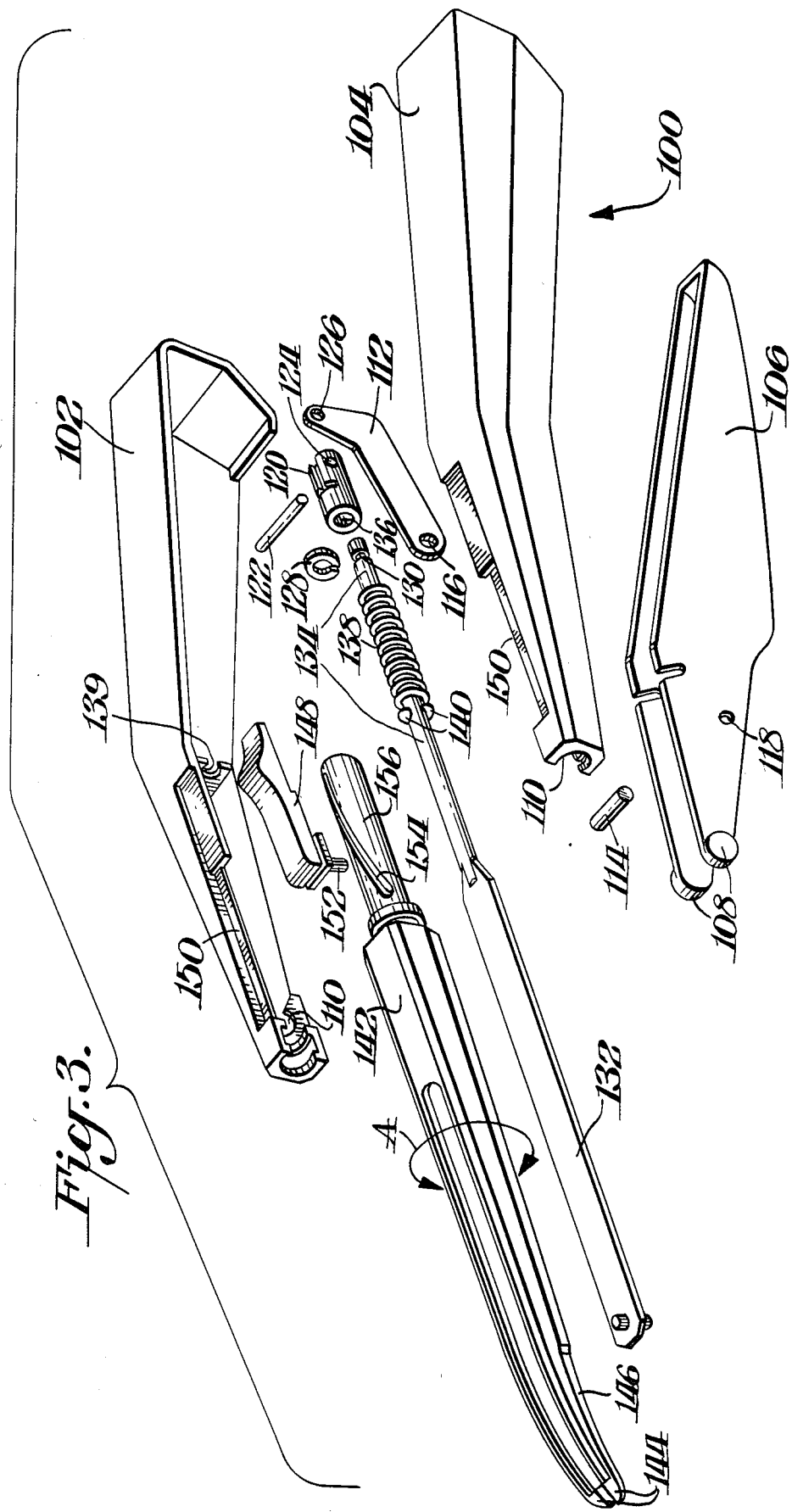
FIG. 3 is an exploded perspective view of the embodiment of FIG. 2.

An exemplary embodiment of the invention is illustrated in FIGS. 2-4, which will be described hereinafter. It should be emphasized that no particular details are either illustrated or described as to the clip magazine, the clip feed mechanism or the like, since these are already known per se from U.S. Pat. No. 4,296,751, from which all such details may be readily obtained. The description and illustration herein are directed strictly to the novel aspects of the present invention; however, to establish a general overview, FIG. 1 has been included.

To establish the differences and similarities between the invention and the device of U.S. Pat. No. 4,296,751, the patented device will first be described.

Figure 1:
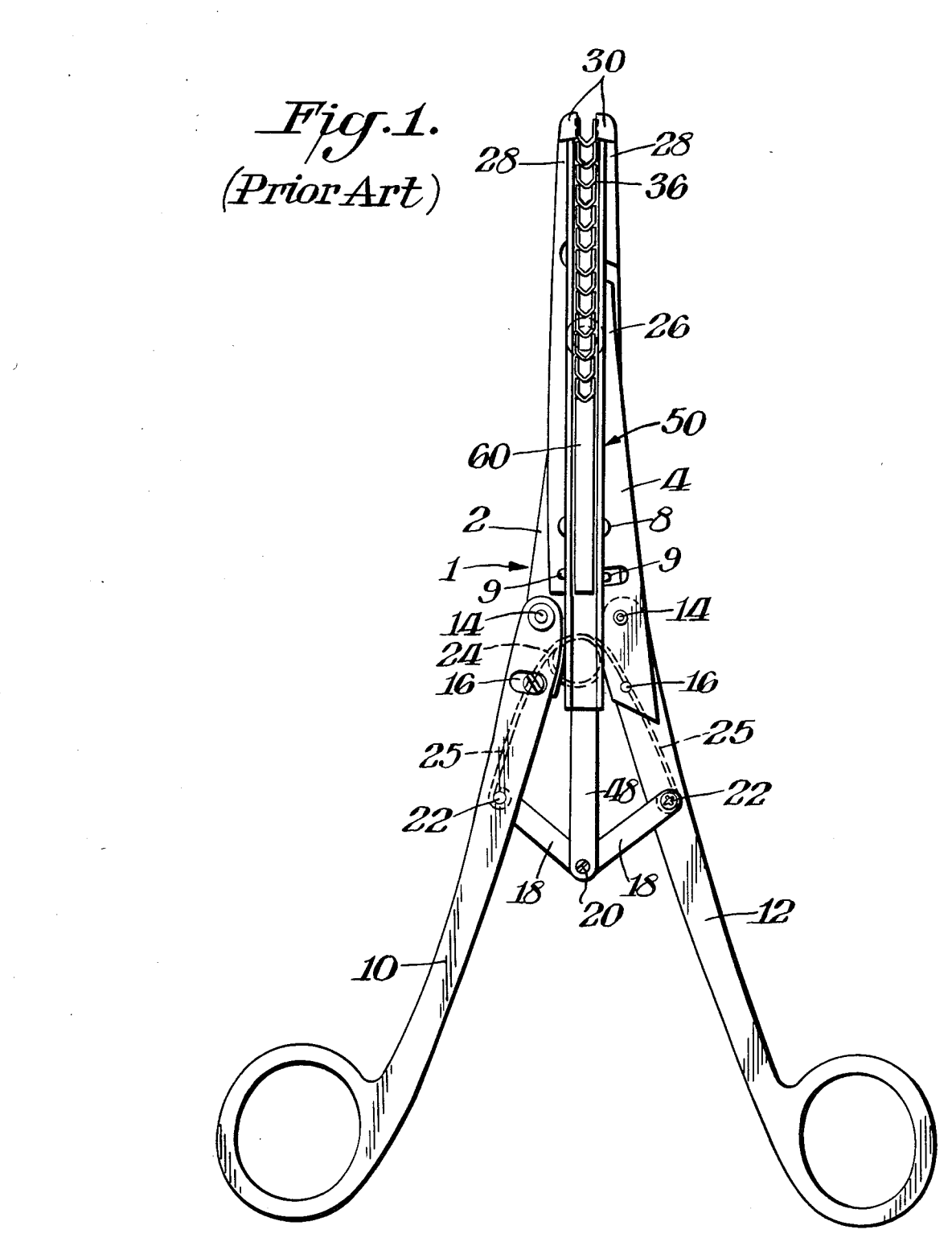

The device in FIG. 1 is constructed as a hemostat forceps and identified in toto with reference numeral 1. It has two arms 2,4 which are pivotally connected by means of a pivot on one and a cooperating transverse slot 8 in the other arm. The arm 4 is also provided with a pair of transversely spaced clip-cartridge retaining and stabilizing stops 9 and with a hole 26 which receives a pivot of the cartridge 50 containing a string of surgical clips 36 which are tracked by a clip retractor 48.

Arms 2,4 have respective handles 10,12, unlike the present invention which utilizes a trigger type mechanism as will be described in detail later on. The handles 10,12 are separate elements pivoted to the arms 2,4 at pivots 14. In addition, each handle 10,12 is connected at the associated arm 2 or 4 via a slot-and-pin connection 16, of which one is shown in detail in FIG. 1. The connection of the pivot and cooperating slot 8 and the connection 16 provide for a lost-motion movement to permit clip retraction when the arms 2,4 are pivoted relative to one another. Subsequently, the end sections 30 of their curved jaws 28 approach one another.

Handles 10,12 are connected by a link 18 having its two bars pivoted to each other at 20 and the opposite sides of handles 10,12 at 22. A torsion spring 24 has two legs 25 connected to the pivots 22 and thus permanently tends to urge the arms 2,4 apart to the FIG. 1 position. Handles 10 and 12 are also urged to the open position.

A modified form of the patented device is described in copending U.S. patent application Ser. No. 313,341, filed Oct. 20, 1981, now U.S. Pat. No. 4,532,925, the details of which are incorporated herein by reference thereto.

The jaws, anvils, clip cartridge, clip advancing and clip retracting mechanism in the device according to the present invention (FIGS. 2-4) may be the same, or substantially the same, as those disclosed in Ser. No. 313,341.

With this in mind, it will be seen from FIGS. 2-4 that one embodiment of the instrument according to the invention is designated in toto by reference numeral 100. It has a casing formed as a handle composed of two shell sections 102 and 104 (compare FIGS. 2 and 3) which are suitably connected, in any manner known per se, to surround the internal mechanism.

That mechanism includes a trigger 106 having stub pivots 108 which are turnably received in mating recesses 110 of shell sections 102 and 104, so that trigger 106 can be angularly displaced about the pivots 108. At least one toggle link 112 is articulated at one end to the trigger 106 by pin 114 which fits into hole 116 in link 112 and holes 118 in trigger 106, and at the other end to a coupling member 120 via a connecting pin 122 which fits into holes 124 of coupling member 120 and hole 126 of link 112. Coupling member 120 is in turn connected via circlip 128 and cooperative groove 130 with an actuating bar or center slide 132, which is disclosed in aforementioned Ser. No. 313,341 and will therefore not be described as to its general construction and function. It is important to note, however, that the rear portion 134 of slide 132 is of circular cross section so that it can turn in the recess 136 of coupling member 120; it will be appreciated that coupling member 120 cannot turn because of the presence of connecting pin 122 and link 112. A helical spring 138 surrounds rear portion 134 in part and bears against abutments 139 formed on shell sections 102,104 and upon abutments 140 formed on rear portion 134.

The instrument further includes a housing or barrel 142 that accomodates the (not illustrated) clip magazine and feeding mechanism, which together constitute the supply means for the clips. Also accomodated in barrel 142, with only their anvils 144 showing, are the jaws 146 which move between an open and a closed position; see U.S. patent application Ser. No. 313,341 in which the anvils cinch the respectively leading clip between them. The essential difference between that construction and the present invention is that in the embodiment herein disclosed, these elements are contained in barrel 142 which is rotatable about its own longitudinal axis, as indicated by the double-headed arrow A. Slide 132 extends into the open rear end of barrel 142 and on into the (not illustrated) cartridge housing where it performs the functions illustrated and discussed in Ser. No. 313,341, which is to say that it cooperates in advancing the string of not-illustrated clips towards anvils 144 when the next clip is being inserted between anvils 144 and thereafter retracting all but the leading clip so that jaws 146 can close and cause anvils 144 to cinch the leading clip between them. For this purpose, slide 132 must also be able to reciprocate lengthwise, which it does every time trigger 106 is pulled and released again.

As a perusal of the aforementioned U.S. patent and application will show, the clips in the magazine are inserted seriatim between anvils 144 of jaws 146. The respectively leading clip (between anvils 144) is then moved into position by the surgeon by holding the tip of the instrument, i.e., where anvils 144 are located, at or near the surgical site. If it is awkward and/or tiring and/or otherwise bothersome for the surgeon to hold the instrument, and thus his hand, in the position best suited to properly apply the leading clip, the invention now makes it possible to change this so-called "presentation" of the clip relative to the surgical site by turning barrel 142, and thereby anvils 144 and the leading clip held between them, in one or the other of the directions indicated by arrow A.

The surgeon must be able to make this change in presentation simply, rapidly and without any real effort if he is to be assisted and relieved in his work by the present invention. Accordingly, the invention makes it possible for him to turn barrel 142 simply by sliding a switch or button 148 forwards or backwards with a finger or thumb of one hand, the backwards or forwards motion being dependent upon whether it is desired to turn barrel 142 in one or in the other direction indicated by arrow A. The edges of switch 148 slide on recessed flanges 150 of a cutout defined by the two shell sections 102,104 and switch 148 is provided, at its underside in the illustrated embodiment, with a connected portion 152 which may be of any desired shape such as spherical. Portion 152 extends into a groove 154 of the rearward extension 156 of barrel 142. The groove 154 extends lengthwise of extension 156 and barrel 142; in addition, however, it also extends circumferentially of extension 156, which is of circular cross section. Consequently, since switch 148 is constrained to perform a linear movement along flanges 150, the portion 152 travelling in groove 154 of extension 156 imposes a turning movement (see arrow A) upon barrel 142 and extension 156. This, then, also changes the presentation (orientation) of anvils 144, and the leading clip held between them, relative to the surgical site without the surgeon having to change the position of his hand.

It is self-evident that this mechanical way of changing the presentation of the leading clip relative to the surgical site can save the surgeon much awkwardness and fatigue, enabling him to perform his task more quickly and accurately. It is further clear that various modifications may be made in the illustrated instrument without in any way departing from the gist of the invention.

One such modification, which is the preferred embodiment, is illustrated in FIGS. 5-6, in which elements corresponding to those shown in FIGS. 2-4 are identified with similar reference numerals as in those figures.

In this modification, trigger 206 has holes 210 which turnably receive stub shafts 208 of shell sections 202 and 204 so that trigger 206 can be angularly displaced about stub shafts 208. Toggle link 212 is articulated at its front end to trigger 206 by pin 214 which fits into hole 216 in link 212 and holes 218 in trigger 206.

The major difference in FIGS. 5-6 is that switch 148 of FIGS. 2-4 is omitted. Instead, the rear end of barrel 242 carries a knurled or otherwise configurated knob or portion 248 which can be secured to, or be of one piece with, barrel 242. What counts is that barrel 242 and knob 248 must turn together and not relative to one another. Thus, in this embodiment, when the user desires to change the presentation of anvils 244 relative to the site, he turns barrel 242, and thereby anvils 244 and the internal mechanism located within barrel 242, by turning knob 248. He can, at least in most instances, do this one-handedly by extending, for example, the index finger of the hand holding the grip of the instrument and using it to turn knob 248.

One further difference in FIGS. 5-6 is the location of the spring 238 which corresponds to spring 138 of FIGS. 2-4. In FIGS. 5-6, spring 238 surrounds a pin-shaped extension 258 of a bifurcated connector 220, corresponding in function to coupling member 120 of FIGS. 2-4, to which link 212 is articulated at its rear end by pin 222 which passes through holes 226 in lever 212 and holes 224 in connector 220. Spring 238 is located in recess 260 of shell section 202 where its rear end bears against a partition wall 262; a similar recess and wall are present in shell section 204, but are not visible in FIG. 5. The two walls 262 are each provided with a cutout 264 which together form an opening through which extension 258 can move rearwardly, relative to spring 238, when the trigger 206 is depressed.

FIGS. 5-6 illustrate the practice of the invention where the turning of barrel 242 is effected by means of circular knob 248 which extends completely around barrel 242 and which is mounted completely externally of the instrument so as to be readily accessible. The concepts of the invention, however, can be practiced in other manners without departing from the spirit of the invention. For example, instead of knob 248, the actuating member might be a lever or handle rigidly connected to barrel 242. The lever or handle could be external of the instrument or could be internally mounted and extend through an arcuate slot in the shell sections. Similarly knob 248 might be internally mounted in the shell sections. The external mounting is preferred, however, since an arcuate slot would limit rotation to less than 360 degrees.

A further noteworthy feature described in detail above is the utilization of the trigger operatively connected to the supply means to effect operation thereof. Preferably, the trigger is at an obtuse angle to the longitudinal axis of the instrument. Such an angle, together with other features such as having the axis of rotation of the clip magazine with its housing coaxial with the instrument's longitudinal axis and using a slidable switch or a knob of circular cross section to rotate the housing, provides an instrument capable of single hand actuation of the jaws and orientation of the clip.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the inventive contribution to the art. Therefore, such adaptations should, and indeed are intended to, be comprehended within the meaning and scope of equivalence of the appended claims.

We claim:

1. A surgical instrument for applying clips to a surgical site, comprising applicator means having a pair of cooperating jaws which are movable between an open and a closed position; supply means for feeding surgical clips to said jaws in a predetermined path for insertion of a clip therebetween while said jaws are in said open position so as to become cinched when said jaws move to said closed position; and mounting means mounting at least part of said supply means for angular displacement about said path so as to vary the orientation at which said clip is being presented to said site, said mounting means comprising a handle and an elongated hollow barrel at least in part accommodating said supply means, said barrel having a longitudinal axis and being mounted in said handle for turning movement relative thereto about said axis, said barrel having a leading end and a trailing end, said trailing end being provided with an extension of circular cross section, said mounting means further including a groove formed in said extension and extending lengthwise and also circumferentially of said axis, and an operating member slidable in said handle lengthwise of said axis and including a connecting portion riding in said groove so that translatory sliding of said slide member lengthwise of said axis is converted into turning movement of said barrel about said axis.

2. A surgical instrument as defined in claim 1, said handle having a cutout extending along said axis and flanked by respective edge portions, and said slide member having lateral marginal portions which rest and slide upon said edge portions.

3. A surgical instrument as defined in claim 2, said handle including a trigger member connected to the handle for displacement relative thereto about a pivot axis which extends crosswise of said longitudinal axis.

4. A surgical instrument for applying clips to a surgical site, comprising applicator means having a pair of cooperating jaws which are movable between an open and a closed position; supply means for feeding surgical clips to said jaws in a predetermined path for insertion of a clip therebetween while said jaws are in said open position so as to become cinched when said jaws move to said closed position; and mounting means mounting at least part of said supply means for angular displacement about said path so as to vary the orientation at which said clip is being presented to said site, said mounting means including a handle, an elongated hollow barrel having a longitudinal axis and being mounted in said handle for turning movement relative thereto about said longitudinal axis, said barrel having an extension of circular cross section at least in part located within said handle, and control means operative at the option of a user for effecting said angular displacement of said barrel, said control means comprising cooperating motion-transmitting portions on said barrel and said handle, respectively, said motion-transmitting portions including a slide member mounted on said handle for translatory movement to and fro along said longitudinal axis.

5. A surgical instrument as defined in claim 4 wherein said slide member has a projection and the other of said motion-transmitting portions is a groove formed in said extension and extending lengthwise of said longitudinal axis as well as being at least in part convoluted thereabout, said projection being slidably engaged in said groove so that translatory movement of said slide member is converted into said angular displacement of said barrel.

6. A surgical instrument as defined in claim 5, said handle having a slot extending lengthwise of said longitudinal axis and said slide member being slideable in said slot.

* * * * *